United States Patent
VanMetter et al.

(10) Patent No.: US 6,351,571 B1
(45) Date of Patent: Feb. 26, 2002

(54) UNIFORM CONVOLUTION ALGORITHM FOR FREQUENCY DECOMPOSITION OF IMAGE REGIONS

(75) Inventors: Richard L. VanMetter, Webster; Kevin S. Kohm, Fairport; Xiaohui Wang, Rochester, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/211,516

(22) Filed: Dec. 14, 1998

(51) Int. Cl.[7] .............................. G06T 5/00; G06T 5/20; G06T 7/00; G06K 9/46; G06K 9/56
(52) U.S. Cl. ..................... 382/254; 382/275; 382/132; 382/191; 382/195; 382/205; 382/206; 382/279
(58) Field of Search ..................... 382/275, 260, 382/263, 264, 266, 269, 274, 205, 128, 132, 279, 191, 195, 206, 254

(56) References Cited

U.S. PATENT DOCUMENTS 4,794,531 A * 12/1988 Morishita et al. ........... 382/132
5,457,754 A * 10/1995 Han et al. ................... 382/128
5,524,162 A *  6/1996 Levien ........................ 382/263

OTHER PUBLICATIONS

"Digital Signal Processing", by Oppenheim and Schafer pp. 105–115, Prentice Hall, Inc., Englewood Cliffs, NJ, 1975.

* cited by examiner

*Primary Examiner*—Scott Rogers
(74) *Attorney, Agent, or Firm*—William F. Noval (57) ABSTRACT

A method of analyzing the low- and high-frequency components of a digital image comprising the steps of: providing a rectangular digital image; specifying the size of a rectangular kernel; partitioning the image into nine sub-regions; processing each of said sub-regions using a unique image processing algorithm; combining said processed sub-regions into a resulting image of the low frequency component and of the original image subtracting the low frequency component from the original image to obtain the high frequency component of said original image.

26 Claims, 5 Drawing Sheets

| 81 | 84 | 63 | 79 | 80 | 68 | 89 | 70 | 63 | 81 | 52 | 67 |
|---|---|---|---|---|---|---|---|---|---|---|---|
| 71 | 84 | 50 | 51 | 52 | 81 | 57 | 84 | 77 | 63 | 64 | 81 |
| 73 | 68 | 50 | 70 | 56 | 64 | 85 | 55 | 66 | 67 | 83 | 78 |
| 52 | 50 | 67 | 70 | 66 | 54 | 89 | 71 | 70 | 86 | 87 | 84 |
| 68 | 87 | 76 | [82] | 71 | 60 | 78 | 63 | 71 | 59 | 56 | 85 |
| 86 | 83 | 67 | 59 | 80 | 65 | 66 | 53 | 52 | 51 | 57 | 68 |
| 66 | 64 | 63 | 76 | 69 | 75 | 78 | 59 | 68 | 53 | 83 | 80 |
| 59 | 56 | 52 | 57 | 64 | 70 | 55 | 66 | 63 | 81 | 66 | 69 |
| 81 | 78 | 71 | 56 | 87 | 69 | 58 | 83 | 53 | 74 | 74 | 63 |
| 83 | 84 | 64 | 62 | 65 | 61 | 53 | 55 | 79 | 78 | 79 | 84 |
| 59 | 81 | 83 | 64 | 75 | 68 | 87 | 52 | 54 | 73 | 88 | 54 |
| 51 | 79 | 53 | 76 | 81 | 60 | 74 | 65 | 66 | 59 | 80 | 79 |

FIG. 4(B)

| 152 | 168 | 113 | 130 | 132 | 149 | 146 | 154 | 140 | 144 | 116 | 148 |
|---|---|---|---|---|---|---|---|---|---|---|---|
| 225 | 236 | 163 | 200 | 188 | 213 | 231 | 209 | 206 | 211 | 199 | 226 |
| 196 | 202 | 167 | 191 | 174 | 199 | 231 | 210 | 213 | 216 | 234 | 243 |
| 193 | 205 | 193 | 222 | 193 | 178 | 252 | 189 | 207 | 212 | 226 | 247 |
| 206 | 220 | 210 | [211] | 217 | 179 | 233 | 187 | 193 | 196 | 200 | 237 |
| 220 | 234 | 206 | 217 | 220 | 200 | 222 | 175 | 191 | 163 | 196 | 233 |
| 211 | 203 | 182 | 192 | 213 | 210 | 199 | 178 | 183 | 185 | 206 | 217 |
| 206 | 198 | 186 | 189 | 220 | 214 | 191 | 208 | 184 | 208 | 223 | 212 |
| 223 | 218 | 187 | 175 | 216 | 200 | 166 | 204 | 195 | 233 | 219 | 216 |
| 223 | 243 | 218 | 182 | 227 | 198 | 198 | 190 | 186 | 225 | 241 | 201 |
| 193 | 244 | 200 | 202 | 221 | 189 | 214 | 172 | 199 | 210 | 247 | 217 |
| 110 | 160 | 136 | 140 | 156 | 128 | 161 | [117] | 120 | 132 | 168 | 133 |

FIG. 4(C)

| 2 | 2 | 2 | 2 | 2 | 2 | 2 | 2 | 2 | 2 | 2 | 2 |
|---|---|---|---|---|---|---|---|---|---|---|---|
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 3 | 3 | 3 | 3 | 3 | 3 | 3 | 3 | 3 | 3 | 3 | 3 |
| 2 | 2 | 2 | 2 | 2 | 2 | 2 | 2 | 2 | 2 | 2 | 2 |

| 320 | 433 | 411 | 375 | 411 | 427 | 449 | 440 | 438 | 400 | 408 | 264 |
|---|---|---|---|---|---|---|---|---|---|---|---|
| 461 | 624 | 599 | 551 | 601 | 632 | 653 | 646 | 626 | 616 | 636 | 425 |
| 398 | 565 | 560 | 532 | 564 | 604 | 640 | 654 | 639 | 663 | 693 | 477 |
| 398 | 591 | 620 | [608] | 593 | 623 | 619 | 648 | 608 | 645 | 685 | 473 |
| 426 | 636 | 641 | 638 | 607 | 629 | 599 | 613 | 576 | 589 | 633 | 437 |
| 454 | 660 | 657 | 643 | 637 | 642 | 597 | 588 | 529 | 550 | 592 | 429 |
| 414 | 596 | 577 | 587 | 615 | 622 | 587 | 560 | 546 | 574 | 608 | 423 |
| 404 | 590 | 573 | 595 | 623 | 625 | 613 | 583 | 600 | 615 | 643 | 435 |
| 441 | 628 | 580 | 578 | 591 | 582 | 570 | 565 | 632 | 647 | 668 | 435 |
| 466 | 684 | 643 | 627 | 607 | 623 | 586 | 574 | 601 | 652 | 667 | 442 |
| 437 | 637 | 646 | 623 | 612 | 624 | 575 | 585 | 581 | 656 | 674 | 464 |
| 270 | 406 | 436 | 432 | 424 | 445 | 406 | 398 | 369 | 420 | 433 | 301 |

FIG. 4(D)

| 4 | 6 | 6 | 6 | 6 | 6 | 6 | 6 | 6 | 6 | 6 | 4 |
|---|---|---|---|---|---|---|---|---|---|---|---|
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 6 | 9 | 9 | 9 | 9 | 9 | 9 | 9 | 9 | 9 | 9 | 6 |
| 4 | 6 | 6 | 6 | 6 | 6 | 6 | 6 | 6 | 6 | 6 | 4 |

FIG. 4(E)

| 80 | 72 | 68 | 62 | 68 | 71 | 74 | 73 | 73 | 66 | 68 | 66 |
|---|---|---|---|---|---|---|---|---|---|---|---|
| 76 | 69 | 66 | 61 | 66 | 70 | 72 | 71 | 69 | 68 | 70 | 70 |
| 66 | 62 | 62 | 59 | 62 | 67 | 71 | 72 | 71 | 73 | 77 | 79 |
| 66 | 65 | 68 | 67 | 65 | 69 | 68 | 72 | 67 | 71 | 76 | 78 |
| 71 | 70 | 71 | 70 | 67 | 69 | 66 | 68 | 64 | 65 | 70 | 72 |
| 75 | 73 | 73 | 71 | 70 | 71 | 66 | 65 | 58 | 61 | 65 | 71 |
| 69 | 66 | 64 | 65 | 68 | 69 | 65 | 62 | 60 | 63 | 67 | 70 |
| 67 | 65 | 63 | 66 | 69 | 69 | 68 | 64 | 66 | 68 | 71 | 72 |
| 73 | 69 | 64 | 64 | 65 | 64 | 63 | 62 | 70 | 71 | 74 | 72 |
| 77 | 76 | 71 | 69 | 67 | 69 | 65 | 63 | 66 | 72 | 74 | 73 |
| 72 | 70 | 71 | 69 | 68 | 69 | 63 | 65 | 64 | 72 | 74 | 77 |
| 67 | 67 | 72 | 72 | 70 | 74 | 67 | 66 | 61 | 70 | 72 | 75 |

FIG. 4(F)

UNIFORM CONVOLUTION ALGORITHM FOR FREQUENCY DECOMPOSITION OF IMAGE REGIONS

FIELD OF THE INVENTION

The present invention relates in general to image enhancement in digital image processing and in particular to a method for rapidly analyzing the high- and low-frequency components of pixels in an arbitrarily shaped region of an image without producing artifacts at edges of the region.

BACKGROUND OF THE INVENTION

It is a common desire to enhance images acquired from imaging devices such as those used for medical imaging diagnostics. Such enhancement may involve amplifying detail and local contrast and sharpening edges. Enhancement algorithms, however, typically produce undesirable artifacts at the edges of the image that result from the analysis of the image into high- and low-frequency components. It is therefore desirable to provide a method for enhancing images while suppressing these artifacts.

Methods for the spatial frequency decomposition of images using the unsharp masking approach have been described by many authors. Two methods for convolution of signals of finite extent, circular convolution and linear convolution, are described by Oppenheim and Schafer ("Digital Signal Processing," pp. 105–113, Prentice Hall, Inc., Englewood Cliffs, N.J., 1975). In circular convolution the image is assumed to be periodic so that for example the pixel to the right of the rightmost pixel is taken to be the leftmost pixel of the same line. This results in image data from the left edge of the image influencing convolutions near the right edge of the image and image data from the bottom of the image influencing convolutions near the top of the image. This can and often results in image artifacts near the edges of the image. Linear convolution takes data outside the image to be of constant value (commonly zero) for purposes of convolution. This causes artifacts within half the kernel width of the edge of the image. Circular and linear convolution are still commonly used.

In many cases the precise method for computing the convolution near the edges of the image is unspecified. This is the case, for example, in the book "Digital Image Processing" by Gonzales and Woods. The descriptions are in terms that are clearly applicable to only the central portion of the image, and not applicable to the edges of the image without further specification.

Therefore the techniques disclosed in these references do not provide a satisfactory solution for efficiently analyzing the high- and low-frequency components of entire images or specified by arbitrary selected regions-of-interest in images. Nor do they address efficient algorithms for these calculations.

SUMMARY OF THE INVENTION

According to the present invention there is provided a method of digital image enhancement, especially image enhancement of medical diagnostic (radiographic) digital images that solves these problems.

According to the feature of the present invention, there is provided a method for efficiently analyzing the low- and high-frequency components of a digital image. The algorithm is first defined in general terms, then specifically for three cases: an entire image, an arbitrarily specified region-of-interest, and an image with multiple arbitrary connected regions of interest.

A specific example is given for the case of the entire image, where the method of the present invention comprises the steps of: providing a rectangular digital image; specifying the size of a rectangular kernel; dividing that rectangular image into nine sub-regions based on the kernel size; applying the modified convolution operator (described herein) in each sub-region; and thereby computing the convolution at each pixel of the original image to obtain the low-frequency component of the original image. The high-frequency component is obtained by subtracting the low-frequency component image from the original image.

For the case of the arbitrarily specified region-of-interest, the method of the present invention comprises the steps of: providing an original digital image and a digital (mask) image describing a region of interest; specifying the size of a rectangular kernel; optionally analyzing the original image to find the smallest rectangle aligned with the pixel coordinates that inscribes the region of interest; dividing that rectangle or the full image into nine sub-regions based on the kernel size; applying the region-of-interest mask-weighted convolution operator (using one of the two methods described below) in each sub-region; and thereby computing the convolution at each pixel of the original image to obtain the low-frequency component of the original image. The high-frequency component is obtained by subtracting the low-frequency component image from the original image.

For the case of the multiple regions of interest, the method of the present invention comprises the steps of: providing an original rectangular digital image; creating an intermediate image for each region of interest of equal size or smaller than the original image; specifying the size of a rectangular kernel; optionally analyzing each intermediate image to find the smallest rectangle aligned with the pixel coordinates that inscribes the region of interest; dividing that rectangle or the full image into nine sub-regions based on the kernel size; applying the region-of-interest mask-weighted convolution operator (using one of the two methods described below) in each sub-region; and thereby computing the convolution at each pixel of the original image to obtain the low-frequency component of the intermediate image. The high-frequency component for each region of interest is obtained by subtracting said low-frequency component image from the intermediate image for that region of interest.

ADVANTAGEOUS EFFECT OF THE INVENTION

The invention has the following advantages.

1. The present invention does not exhibit edge profile artifacts near the borders since only original image pixels within the kernel are used to compute the convolution.

2. No arbitrary pixel value need be assumed for "padding" the image and image data from the opposite border is not included in the calculation.

3. The present invention is capable of limiting the computation of the convolution to any arbitrarily shaped region of interest or to a region of interest described by a convex hull. In the former case it only requires that the region be defined by a "mask" image. In the latter, the convex hull must be described.

4. The methods described in the present invention avoid the artifacts associated with the edges of the region of interest and can speed the computation as a smaller area is used for the convolution.

DETAILED DESCRIPTION OF THE INVENTION

Figure 2:
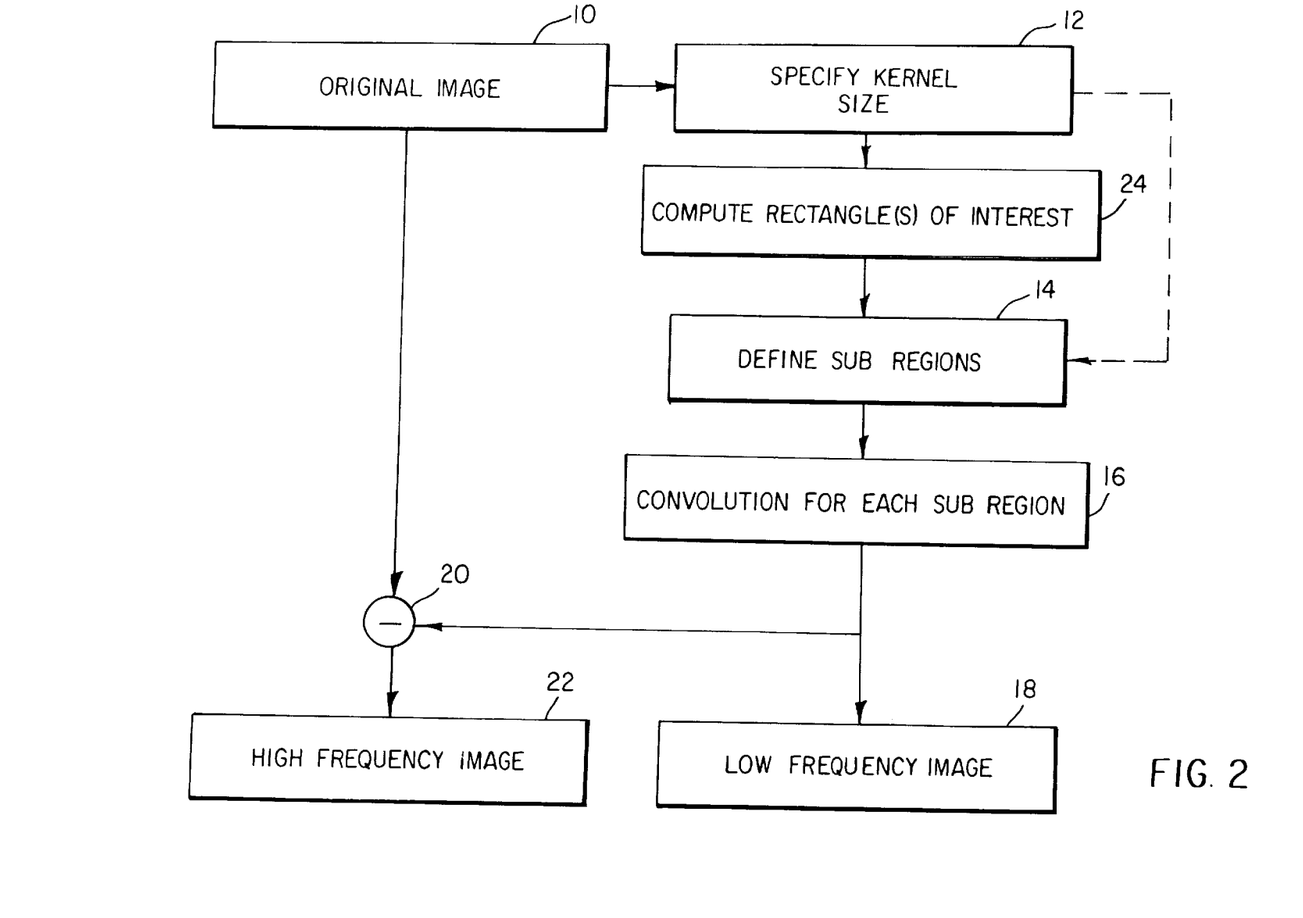
FIG. 2 is a flow diagram of the method of the present invention.

Referring now to FIG. 2, there is shown a flow diagram of the method of the present invention. As shown, an original rectangular digital image is provided (box 10). Next, the rectangular kernel size is specified (box 12). If the entire original image is to be processed, then the image is divided into nine sub-regions based on the kernel size (box 14). Each sub-region is applied a modified convolution operator (box 16). The convolution of each pixel of the original image is computed to obtain the low frequency component of the original image (box 18). The low frequency component image is subtracted from the original image (operator 20) to obtain the high frequency component image (box 22).

If the one or more arbitrarily specified region of interests are selected, then the further step of computing the rectangle (s) of interest is(are) carried out (box 24). The remaining steps are then carried out on each rectangle of interest.

Figure 3:
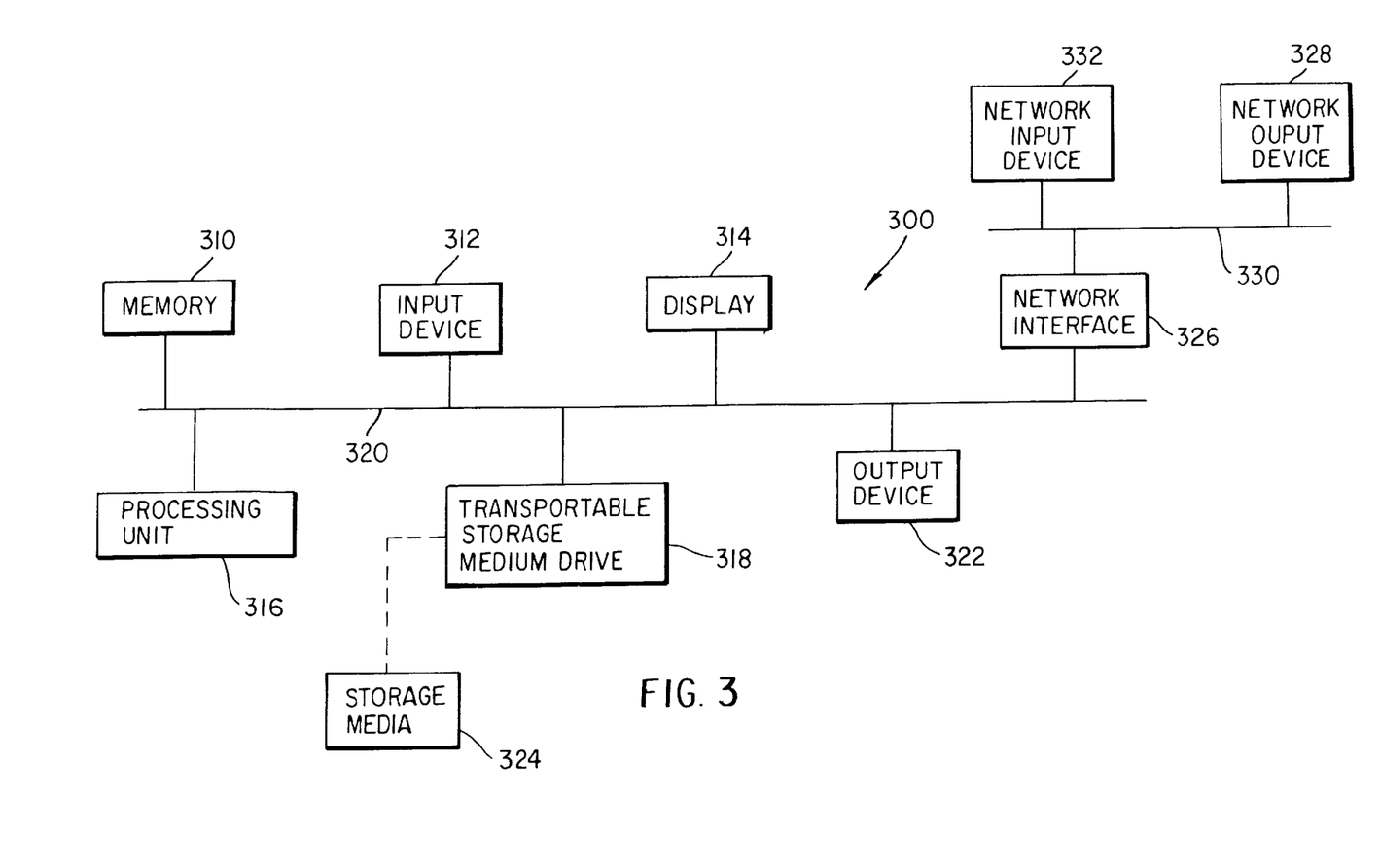
FIG. 3 is a block diagram of image processing apparatus for carrying out the method of the present invention.

The digital image is processed in an image processor, according to the method of the present invention. The image processor can take the form of a digital computer, such as illustrated in FIG. 3. In such case, one or more of the steps of said method can be carried out using software routines. The image processor can also include hardware or firmware for carrying out one or more of said method steps. Thus, the steps of the method of the invention can be carried out using software, firmware, and hardware, either alone or in any preferable combination.

As shown in FIG. 3, a digital computer 300 includes a memory 310 for storing digital images, application programs, operating system, etc. Memory 310 can include mass memory (such as a hard magnetic disc or CD ROM), and fast memory (such as RAM). Computer 300 also includes input device 312 (such as a keyboard, mouse, touch screen), display 314 (CRT monitor, LCD), central processing unit 316 (microprocessor). Components 310, 312, 314, 316 are connected together by control/data bus 320. Computer 300 can include a transportable storage medium drive 318 for reading from and/or writing to transportable storage media 324, such as a floppy magnetic disk or writeable optical compact disk (CD). Computer 300 can include a computer network interface 326 for reading from and/or writing to the computer network 330, in which case the network interface 326 is connected to the control/data bus 320. Computer 300 can include a directly connected output device 322 (thermal printer, dot matrix printer, laser printer, ink jet printer) and/or a computer network 300 connected output device 328. Computer 300 can include an input device 332 which is connected to the computer network.

As used in this application, computer readable storage medium can include, specifically, memory 310 and transportable storage medium 324. More generally, computer storage medium may comprise, for example, magnetic storage media, such as magnetic disk (hard drive, floppy disk) or magnetic tape; optical storage media, such as optical disk, optical tape, or machine readable barcode; solid state electronic storage devices, such as random access memory (RAM), read only memory (ROM); or any other physical device or medium which can be employed to store a computer program.

The algorithm may be defined in general as follows. An rectangular image is provided with pixel coordinates ranging from (0,0) to $(x_{max}, y_{max})$. A uniform rectangular kernel is specified with size, $K_x$ by $K_y$. Calculation of the low-frequency image is as follows. For each image pixel (x,y) within the input image, sum all image pixels included in the rectangular region $(\max(x-K_x/2, 0), \max(y-K_y/2, 0))$ to $(\min(x+K_x/2, x_{max}), \min(y+K_y/2, y_{max}))$ and divide this sum by the total number of pixels included in the sum. The high frequency output image is calculated by subtracting the low frequency component from the original image. If a region of interest mask is supplied along with the image, the calculation of the low-frequency image is modified as follows. For each image pixel (x,y) within the image, sum all image pixels included in the union of the region of interest and the rectangular region $(\max(x-K_x/2, 0), \max(y-K_y/2, 0))$ to $(\min(x+K_x/2, x_{max}), \min(y+K_y/2, y_{max}))$ then divide the sum by the total number of pixels included in the sum. The high frequency output image is calculated by subtracting the low frequency component from the original image.

Figure 1:
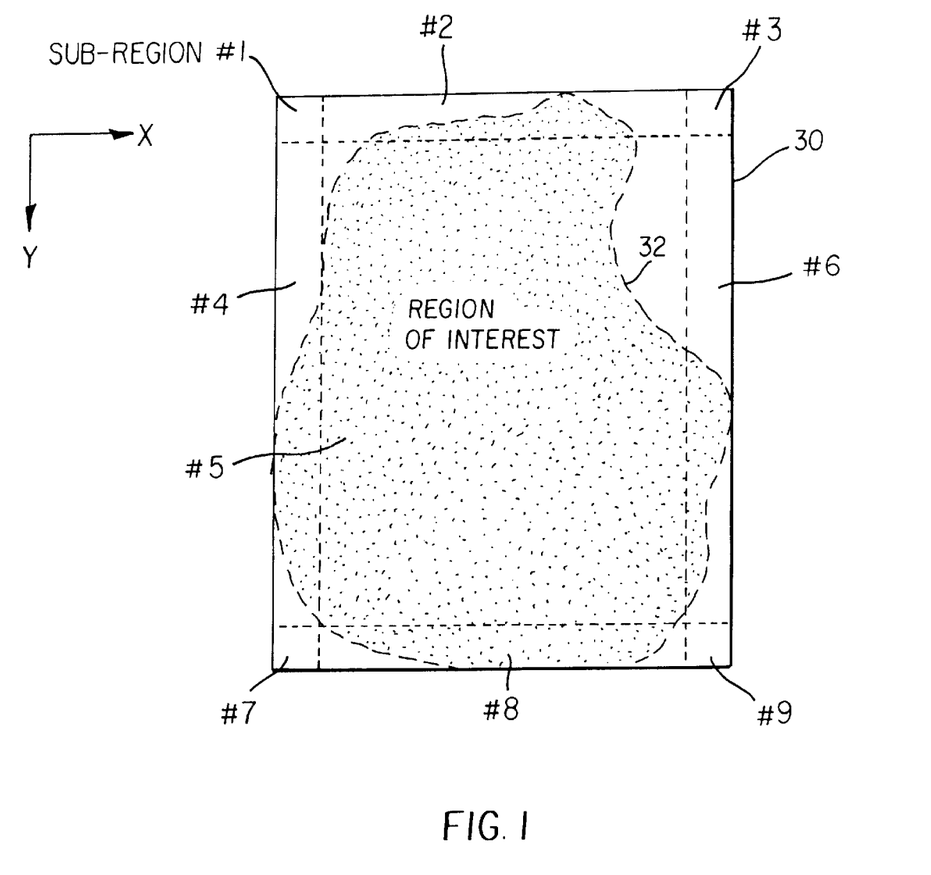
FIG. 1 is a diagrammatic view which shows the nine sub-regions of the rectangle-of-interest enclosing a regionof-interest within an image. The rectangle of interest may be the entire image or a sub-image of the entire image. The region-of-interest may be an arbitrary connected region of the entire image.

FIG. 1 illustrates the step of analyzing the original image for the smallest rectangle 30 bounding an irregular region of interest. An exemplary division of rectangle 30 into nine sub-regions 1–9 is also illustrated.

Following is a detailed description of a specific implementation of the present invention.

1. Spatial Frequency Decomposition of an Entire Rectilinear Image

The unsharp mask of an image is computed as follows. An image, I(x,y) is provided that is defined for a rectangular region having corners at (0,0), and $(x_{max}, y_{max})$.

The rectangle-of-interest is divided into nine sub-regions. These are defined as follows:

Sub-region #1: (0,0) to (K/2,K/2).
Sub-region #2: (K/2+1,0) to $(x_{max}-K/2-1, K/2)$.
Sub-region #3: $(x_{max}-K/2, 0)$ to $(x_{max}, K/2)$.
Sub-region #4: (0,K/2+1) to $(K/2, y_{max}-K/2-1)$.
Sub-region #5: (K/2+1,K/2+1) to $(x_{max}-K/2-1, y_{max}-K/2-1)$.
Sub-region #6: $(x_{max}-K/2, K/2+1)$ to $(x_{max}, y_{max}-K/2-1)$.
Sub-region #7: $(0, y_{max}-K/2)$ to $(K/2, y_{max})$.
Sub-region #8: $(K/2+1, y_{max}-K/2)$ to $(x_{max}-K/2-1, y_{max})$.
Sub-region #9: $(x_{max}-K/2, y_{max}-K/2)$ to $(x_{max}, y_{max})$.

where K is an odd integer specifying the width of the kernel in pixels and K/2 is truncated to an integer. The algorithm for computing the modified convolution is slightly different in each sub-region and is described as follows.

a. Sub-Regions #1, #2 and #3:

Vertical image sum buffers are created for each pixel in the first row of the rectangle-of-interest. The vertical image sum buffer for each column of the image is initialized to the sum of the first K/2 image pixels in that column.

Prior to the calculations for each row in the sub-regions #1, #2 and #3 the vertical image sum buffers are augmented by the image value for that pixel in row y+K/2.

a.1. Sub-Region #1

The image accumulator is initialized to the sum of the first K/2+1 vertical image sum buffers. The pixel count accumulator is initialized to (K/2+1)*(K/2+1). The output image at the first pixel is the value of the image accumulator divided by the value of the pixel count accumulator.

For each subsequent pixel in the line the value of the $x+K/2$ vertical image sum buffer is added to the image accumulator and $K/2+1+y$ is added to the pixel count accumulator. The output image is the value of the image accumulator divided by the value of the pixel count accumulator.

a.2. Sub-Region #2

At each successive pixel the value of the $x+K/2$ vertical image sum buffer is added and the value of the $x-K/2-1$ vertical image sum buffer is subtracted from the image accumulator. The pixel count accumulator is unchanged. The output image is the value of the image accumulator divided by the value of the pixel count accumulator.

a.3 Sub-Region #3

At each successive pixel the value of the $x-K/2-1$ vertical image sum buffer is subtracted from the image accumulator and $K/2+1+y$ is subtracted from the pixel count accumulator. The output image is the value of the image accumulator divided by the value of the pixel count accumulator.

b. Sub-Regions #4, #5, and #6

The calculations for these regions are the same as those for regions #1, #2, and #3, respectively, with the following exception. Prior to the calculations for each row in the sub-regions #4, #5 and #6 the vertical image sum buffers are augmented by image pixel value in row $y+K/2$ and reduced by the image pixel value in row $y-K/2-1$. The pixel count accumulator is adjusted appropriately in each of the three sub-regions.

c. Sub-Regions #7, #8, and #9

The calculations for these regions are the same as those for regions #1, #2, and #3, respectively, with the following exception; prior to the calculations for each row in the sub-regions #7, #8 and #9 the vertical image sum buffers are reduced by the image pixel value in row $y-K_y/2-1$.

c.1 Sub-Region #7:

The image accumulator is initialize to the sum of the first $K_x/2+1$ vertical image sum buffers. The pixel count accumulator is initialized to $(y_{max}-y+K_y/2+1)*(K_x/2+1)$. The output image at the first pixel is the value of the image accumulator divided by the value of the pixel count accumulator. For pixel x in each line the value of the $x+K_x/2+1$ vertical image sum buffer is added to the image accumulator and the pixel count accumulator is incremented by $y_{max}-y+K_y/2+1$ to reflect the total number of pixels contributing to the convolution.

c.2. Sub-Region #8:

At each successive pixel the value of the $x+K_x/2$ vertical image sum buffer is added and the value of the $x-K_x/2-1$ vertical image sum buffer is subtracted from the image accumulator; the pixel count accumulator is unchanged; the output image is the value of the image accumulator divided by the value of the pixel count accumulator.

c.3. Sub-Region #9:

At each successive pixel the value of the $x-K_x/2-1$ vertical image sum buffer is subtracted from the image accumulator and $y_{max}-y+K_y/2+1$ is subtracted from the pixel count accumulator; the output image is the value of the image accumulator divided by the value of the pixel count accumulator.

The output image is a low-pass filtering of the original image. A high-pass image is obtained by subtracting the low-pass image from the original image.

2. Spatial Frequency Decomposition of an Arbitrary Connected Region of Interest/method 1.

The unsharp mask of an arbitrary region of interest is computed as follows. An image, $I(x,y)$, containing a region of interest and a mask, $M(x,y)$, delineating that region of interest are provided. The region of interest mask is searched to find the first line ($y_{min}$) and last image line ($y_{max}$) within the region of interest as well as the first pixel ($x_{min}$) and last pixel ($x_{max}$) on any line within the region of interest. These then define a rectangle-of-interest that includes the entire region of interest having corners at ($x_{min},y_{min}$), and ($x_{max},y_{max}$).

The rectangle-of-interest is divided into nine sub-regions. These are defined as follows:

Sub-region #1: ($x_{min},y_{min}$) to ($x_{min}+K/2,y_{min}+K/2$).

Sub-region #2: ($x_{min}+K/2+1,y_{min}$) to ($x_{max}-K/2-1,y_{min}+K/2$).

Sub-region #3: ($x_{max}-K/2,y_{min}$) to ($x_{max},y_{min}+K/2$).

Sub-region #4: ($x_{min},y_{min}+K/2+1$) to ($x_{min}+K/2,y_{max}-K/2-1$).

Sub-region #5: ($x_{min}+K/2+1,y_{min}+K/2+1$) to ($x_{max}-K/2-1,y_{max}-K/2-1$).

Sub-region #6: ($x_{max}-K/2,y_{min}+K/2+1$) to ($x_{max},y_{max}-K/2-1$).

Sub-region #7: ($x_{min},y_{max}-K/2$) to ($x_{min}+K/2,y_{max}$).

Sub-region #8: ($x_{min}+K/2+1,y_{max}-K/2$) to ($x_{max}-K/2-1,y_{max}$).

Sub-region #9: ($x_{max}-K/2,y_{max}-K/2$) to ($x_{max},y_{max}$).

where K is an odd integer specifying the width of the kernel in pixels and K/2 is truncated to an integer. The algorithm for computing the modified convolution is slightly different in each sub-region and is described as follows.

a. Sub-Regions #1, #2 and #3:

Vertical pixel count buffers are created for each pixel in the first row of the rectangle-of-interest. The vertical pixel count buffer for each column of the image is initialized to the sum of the first K/2 mask pixels in that column. Mask pixels are one within the region of interest and zero otherwise. Vertical image sum buffers are created for each pixel in the first row of the rectangle-of-interest. The vertical image sum buffer for each column of the image is initialized to sum of the product of the first K/2 image pixels in that column each multiplied by the respective mask image value.

Prior to the calculations for each row in the sub-regions #1, #2 and #3 the vertical pixel count buffers are augmented by the mask value for that pixel in row $y+K/2$ and the vertical image sum buffers are augmented by the product of the image and the mask for that pixel in row $y+K/2$.

a.1. Sub-Region #1

The image accumulator is initialize to the sum of the first K/2+1 vertical image sum buffers. The pixel count accumulator is initialized to the sum of the first K/2+1 vertical pixel count buffers. The output image at the first pixel is the value of the image accumulator divided by the value of the pixel count accumulator.

For pixel x in each line the $x+K/2$ vertical image sum buffer and the $x+K/2$ vertical pixel count buffer are added to their respective accumulators. The output image is the value of the image accumulator divided by the value of the pixel count accumulator.

a.2. Sub-Region #2

At each successive pixel the $x+K/2$ vertical image sum buffer and the $x+K/2$ vertical pixel count buffer are added to their respective accumulators. The $x-K/2-1$ vertical image sum buffer and the $x-K/2-1$ vertical pixel count buffer are subtracted from their respective accumulators. The output image is the value of the image accumulator divided by the value of the pixel count accumulator.

a.3 Sub-Region #3

At each successive pixel the x−K/2−1 vertical image sum buffer and the x−K/2−1 vertical pixel count buffer are subtracted from their respective accumulators. The output image is the value of the image accumulator divided by the value of the pixel count accumulator.

b. Sub-Regions #4, #5, and #6

The calculations for these regions are the same as those for regions #1, #2, and #3, respectively, with the following exception.

Prior to the calculations for each row in the sub-regions #4, #5 and #6 the vertical pixel count buffers are augmented by the mask value for that pixel in row y+K/2 and reduced by the mask value for that pixel in row y+K/2−1. Similarly, the vertical image sum buffers are augmented by the product of the image and the mask for that pixel in row y+K/2 and reduced by the product of the image and the mask for that pixel in row y−K/2−1.

c. Sub-Regions #7, #8, and #9

The calculations for these regions are the same as those for regions #1, #2, and #3, respectively, with the following exception.

Prior to the calculations for each row in the sub-regions #7, #8 and #9 the vertical pixel count buffers are reduced by the mask value for that pixel in row y−K/2−1. Similarly, the vertical image sum buffers are reduced by the product of the image and the mask for that pixel in row y−K/2−1.

3. Spatial Frequency Decomposition of an Arbitrary Connected Region of Interest/method 2.

The unsharp mask of an arbitrary region of interest is computed as follows. An image, I(x,y), containing a region of interest and a mask, M(x,y), delineating that region of interest are provided. The region of interest mask, M(x,y) is applied to the image, I(x,y) so that all pixels outside the region of interest are set to zero and all pixels inside the region of interest are unchanged. Optionally, the image is searched to find the first line ($Y_{min}$) and last image line ($y_{max}$) within the region of interest as well as the first pixel ($x_{min}$) and last pixel ($x_{max}$) on any line within the region of interest. These then define a rectangle-of-interest that includes the entire region of interest having corners at ($X_{min}, y_{min}$), and ($X_{max}, y_{max}$).

The rectangle-of-interest is divided into nine sub-regions. These are defined as follows:

Sub-region #1: ($X_{min}, y_{min}$) to ($x_{min}$+K/2, $y_{min}$+K/2).

Sub-region #2: ($x_{min}$+K/2+1, $y_{min}$) to ($x_{max}$−K/2−1, $y_{min}$+K/2).

Sub-region #3: ($x_{max}$−K/2, $y_{min}$) to ($x_{max}$, $y_{min}$+K/2).

Sub-region #4: ($x_{min}$, $y_{min}$+K/2+1) to ($x_{min}$+K/2, $y_{max}$−K/2−1).

Sub-region #5: ($x_{min}$+K/2+1, $y_{min}$+K/2+1) to ($x_{max}$−K/2−1, $y_{max}$−K/2−1).

Sub-region #6: ($x_{max}$−K/2, $y_{min}$+K/2+1) to ($x_{max}$, $y_{max}$−K/2−1).

Sub-region #7: ($x_{min}$, $y_{max}$−K/2) to ($x_{min}$+K/2, $y_{max}$).

Sub-region #8: ($x_{min}$+K/2+1, $y_{max}$−K/2) to ($x_{max}$−K/2−1, $y_{max}$).

Sub-region #9: ($x_{max}$−K/2, $y_{max}$−K/2) to ($x_{max}, y_{max}$).

where K is an odd integer specifying the width of the kernel in pixels and K/2 is truncated to an integer. The algorithm for computing the modified convolution is slightly different in each sub-region and is described as follows.

a. Sub-Regions #1, #2 and #3:

Vertical pixel count buffers are created for each pixel in the first row of the rectangle-of-interest. The vertical pixel count buffer for each column of the image is initialized to sum of the first K/2 mask pixels in that column. Mask pixels are one within the region of interest and zero otherwise. Vertical image sum buffers are created for each pixel in the first row of the rectangle-of-interest. The vertical image sum buffer for each column of the image is initialized to the sum the first K/2 image pixels in that column.

Prior to the calculations for each row in the sub-regions #1, #2 and #3 the vertical pixel count buffers are augmented by the mask value for that pixel in row y+K/2 and the vertical image sum buffers are augmented by the value of the image pixel in row y+K/2.

a.1. Sub-Region #1.

The image accumulator is initialize to the sum of the first K/2+1 vertical image sum buffers. The pixel count accumulator is initialized to the sum of the first K/2+1 vertical pixel count buffers. The output image at the first pixel is the value of the image accumulator divided by the value of the pixel count accumulator.

For pixel x in each line the x+K/2 vertical image sum buffer and the x+K/2 vertical pixel count buffer are added to their respective accumulators. The output image is the value of the image accumulator divided by the value of the pixel count accumulator.

a.2. Sub-Region #2

At each successive pixel the x+K/2 vertical image sum buffer and the x+K/2 vertical pixel count buffer are added to their respective accumulators. The x−K/2−1 vertical image sum buffer and the x−K/2−1 vertical pixel count buffer are subtracted from their respective accumulators. The output image is the value of the image accumulator divided by the value of the pixel count accumulator.

a.3 Sub-Region #3

At each successive pixel the x−K/2−1 vertical image sum buffer and the x−K/2−1 vertical pixel count buffer are subtracted from their respective accumulators. The output image is the value of the image accumulator divided by the value of the pixel count accumulator.

b. Sub-Regions #4, #5, and #6

The calculations for these regions are the same as those for regions #1, #2, and #3, respectively, with the following exception.

Prior to the calculations for each row in the sub-regions #4, #5 and #6 the vertical pixel count buffers are augmented by the mask value for that pixel in row y+K/2 and reduced by the mask value for that pixel in row y−K/2−1. Similarly, the vertical image sum buffers are augmented by the value of the image pixel in row y+K/2 and reduced by the value of the image pixel in row y−K/2−1.

c. Sub-Regions #7, #8 and #9

The calculations for these regions are the same as those for regions #1, #2, and #3, respectively, with the following exception.

Prior to the calculations for each row in the sub-regions #7, #8 and #9 the vertical pixel count buffers are reduced by the mask value for that pixel in row y−K/2−1. Similarly, the vertical image sum buffers are reduced by the value of the image pixel in row y−K/2−1.

FIGS. 4A–4F illustrate an example of the present invention.

The example shows an example calculation based on the invention. An image is represented as a 12×12 matrix of digital code values. The kernel size in this example has been taken to be 3 pixels × 3 pixels. In this example, the horizontal rows and vertical columns of the image are numbered from 0 to 11. Note that all calculations use integer arithmetic wherein the fractional parts of quotients are truncated.

Figure 4A:
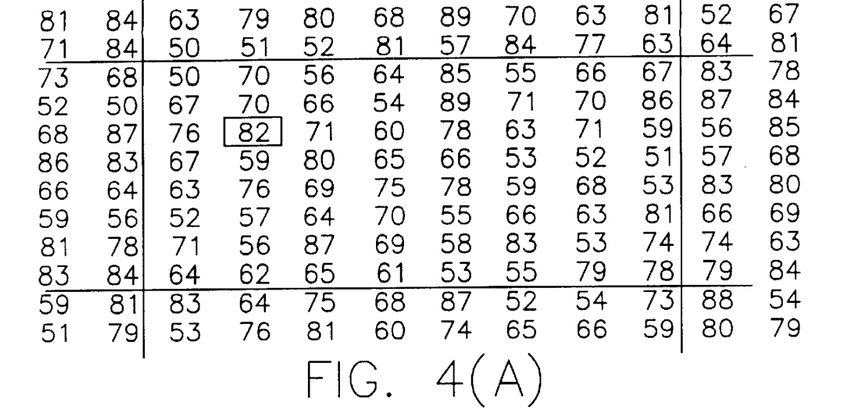
FIGS. 4(A)–4(F) are diagrammatic views illustrating the present invention.

FIG. 4(A) represents an input image to the algorithm. The solid lines divide the nine sub-regions of the image that are defined in the invention. For example, in this case, sub-region #1 is the rectangular region from pixel (0,0) up to and including pixel (K/2,K/2). The kernel size, K=3, hence by integer arithmetic K/2=1. Therefore, sub-region #1 is from (0,0) up to and including (1,1) which includes the pixels at (0,0), (0,1), (1,0) and (1,1). The other sub-regions are defined similarly.

Figure 4B:
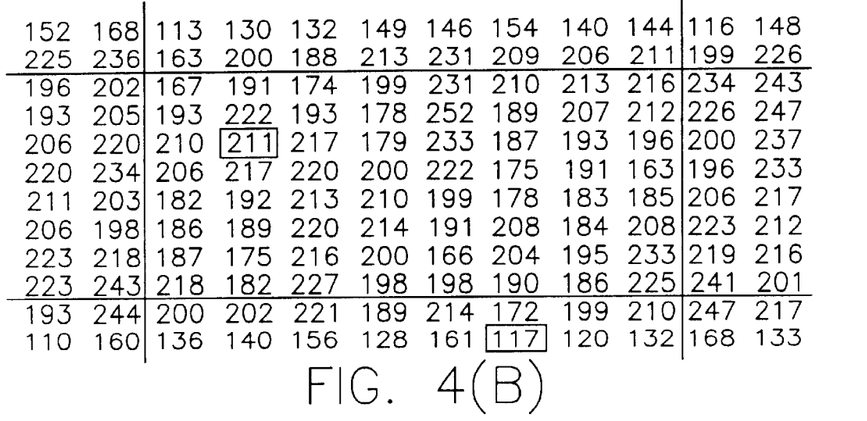

FIG. 4(B) represents the numerical values stored in the vertical sum buffers defined above. Following that definition, the vertical sum buffers for the first row are initialized to the sum of the first (K/2+1)=(3/2+1)=2 image elements in their respective column. For example, in the first column of the first row, the sum of the first two rows of the first column of the input image are summed 81+71=152. The vertical sum buffer in each of the other columns is initialized similarly. The vertical sum buffers for the second row are computed by adding the pixel value in the third row of that column to the previous vertical sum buffer for that column. Thus, in the first column, the pixel value 73 is added to the previous vertical sum buffer 152 to obtain 225. The same calculation is followed in sub-regions #1, #2, and #3. In sub-regions #4, #5, and #6, the value of one pixel is added and that of one pixel is subtracted from each previous vertical sum buffer. Consider the vertical sum buffer at pixel (3,4) outlined with the dotted line. The previous vertical sum buffer in that column, 22, is augmented by 59, the pixel value at (3,5) and reduced by 70, the pixel value at (3,2). The result is 222+59−70=211. In sub-regions #7, #8, and #9, the value of one pixel is subtracted from the previous vertical sum buffer in each column. For example, consider the vertical sum buffer at pixel (7,11) outlined with the dotted line. The previous vertical sum buffer in that column, 172, is reduced by 55, the pixel value at (7,9). The result is 172−55=117.

Figure 4C:
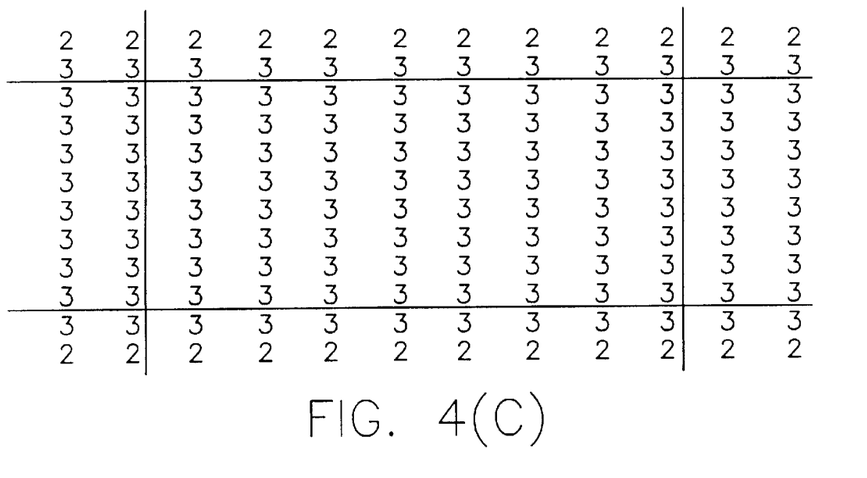

FIG. 4(C) represents the numerical values stored in the vertical count buffers defined above. This is the number of pixels that contribute to the corresponding element of the vertical sum buffers shown in FIG. 4(B). For example, in the first column of the first row, the number of elements of the original image contributing to the vertical sum buffer is 2. In each column of subsequent rows, 3 pixels contribute except the last where again 2 pixels contribute. In practice, the values of the vertical count buffers are calculated in a similar way to those of the vertical sum buffers. The difference is that instead of adding or subtracting the value for pixels, the number of pixels is used. In sub-regions #1, #2, and #3 of this example, the vertical count buffers in each row are simply one more than that in the previous row. In sub-regions #4, #5, and #6, the vertical count buffers are unchanged. In sub-regions #7, #8, and #9, the vertical count buffers are decremented from that in the previous row in that region.

Figure 4D:
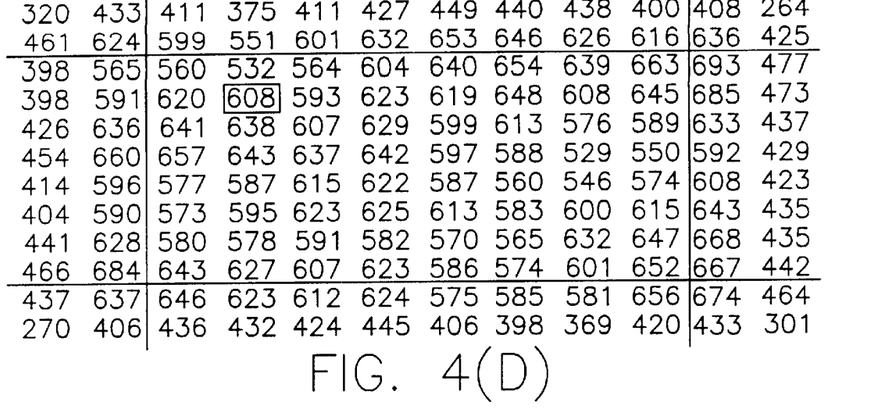

FIG. 4(D) represents the image accumulator. The image accumulator is the sum of the vertical sum buffers contributing to the output image at any pixel. The image accumulator for the first column of each row is initialized to the sum of the first (K/2+1) vertical sum buffers in that row. For example, in the first column of the fourth row, the image accumulator is initialized to 193+205=398, the sum of the first two vertical sum accumulators in that row. For other columns of regions #1, #4, and #7, the value of the image accumulator from the previous column is augmented by the value of the vertical sum accumulator (K/2) columns to the right. For example, the image accumulator for pixel (1,6) is the sum of 414, the image sum buffer at pixel (0,6) and 182, the vertical sum buffer at pixel (2,6). In sub-regions #2, #5, and #8, the value of the image accumulator from the previous column is augmented by the value of the vertical sum accumulator (K/2) columns to the right and reduced by the value of the vertical sum accumulator (K/2+1) columns to the left. For example, the image accumulator for pixel (3,3) is the sum of 620, the image sum buffer at pixel (2,3) plus 193, the vertical sum buffer at pixel (4,3) minus 205, the vertical sum buffer at pixel (1,3).

Figure 4E:
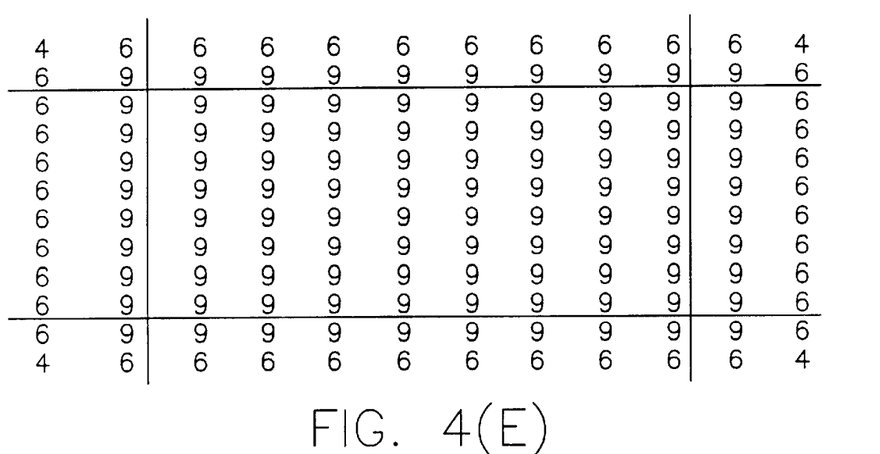

FIG. 4(E) represents the count accumulator defined above. This is the number of pixels that contribute to the corresponding element of the image accumulator shown in FIG. 4(D). For example, in the first column of the first row, the number of elements of the original image contributing to the image accumulator is 4. In practice, the values of the count accumulator are calculated in a similar way to those of the image accumulator. The difference is that instead of adding or subtracting values from the vertical sum buffers, the values from the vertical count buffers are used.

Figure 4F:
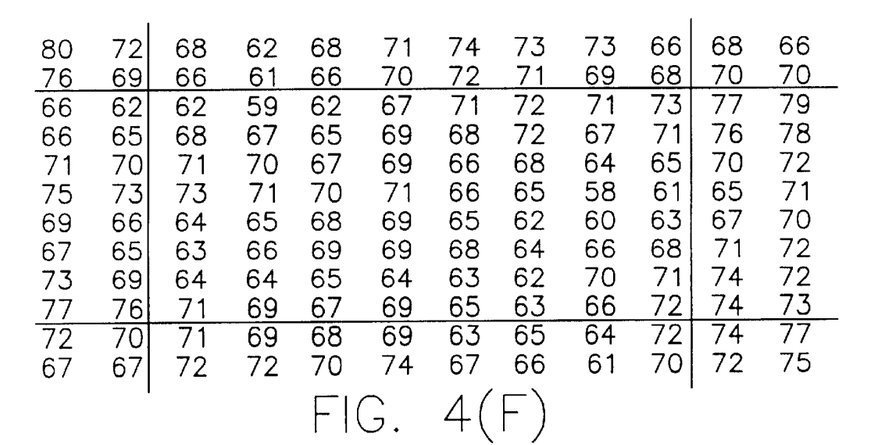

FIG. 4(F) represents the output image for this simple example. At each pixel, the output image is the quotient of the image accumulator dividend by the count accumulator. For example, the value of 68 at pixel (2,3) is obtained as the quotient of 620, the corresponding value of the image accumulator divided by 9, the corresponding value of the count accumulator.

The invention has been described in detail with particular reference to certain preferred embodiments thereof, but it will be understood that variations and modifications can be effected within the spirit and scope of the invention.

PARTS LIST

10 original image
12 kernel size specified
14 sub-regions defined
16 convolution for each sub-region
18 low frequency image
20 low frequency image subtracted from original image
22 high frequency image
24 compute rectangle(s) of interest
300 digital computer
310 memory
312 input device
314 display
316 central processing unit
318 output device
320 control/data bus
322 output device
324 transportable storage media
326 network interface
328 network output device
330 computer network
332 network input device

What is claimed is:
1. A method of analyzing the low- and high-frequency components of a digital image comprising the steps of:
   providing a rectangular digital image with pixel coordinates ranging from (0,0) to $(x_{max}, y_{max})$;
   specifying the size of a rectangular kernel, $K_x$ by $K_y$;
   processing the image as follows:
      for each image pixel (x,y) within the image, sum all image pixels included in the rectangular region (max$(x-K_x/2,0)$, max$(y-K_y/2,0)$) to (min$(x+K_x/2,x_{max})$, min$(y+K_y/2,y_{max})$) and divide said sum by the total number of pixels included in said sum, the result is the low frequency component pixel (x,y) in the low-frequency image;

subtracting said low-frequency component from said provided digital image to obtain the high frequency component of said provided digital image.

2. A method of analyzing the low- and high-frequency components of a digital image comprising the steps of:
providing a rectangular digital image with pixel coordinates ranging from (0,0) to $(x_{max}, y_{max})$;
defining a region of interest within said image;
specifying the size of a rectangular kernel, $K_x$ by $K_y$;
processing the image as follows:
for each image pixel (x,y) within the image, sum all image pixels included in the union of the region of interest and the rectangular region $(max(x-K_x/2, 0), max(y-K_y/2,0))$ to $(min(x+K_x/2,x_{max}), min(y+K_y/2,y_{max}))$ then divide said sum by the total number of pixels included in said sum, the result is the low frequency component output pixel (x,y);
subtracting said low-frequency component from said original image to obtain the high frequency component of said original image.

3. A method of analyzing the low- and high-frequency components of a digital image comprising the steps of:
providing a rectangular digital image;
specifying the size of a rectangular kernel;
partitioning the image into nine sub-regions based on the size of said kernel and said digital image;
processing each of said sub-regions using a unique image processing algorithm;
combining said processed sub-regions into a resulting image of the low frequency component of the original image, and subtracting the low frequency component from the original image to obtain the high frequency component of said original image.

4. The method of claim 3 wherein each sub-region in said partitioning step is defined as follows:
Sub-region #1: (0,0) to $(K_x/2,K_y/2)$;
Sub-region #2: $(K_x/2+1,0)$ to $(x_{max}-K_x/2-1,K_y/2)$;
Sub-region #3: $(x_{max}-K_x/2,0)$ to $(x_{max},K_y/2)$;
Sub-region #4: $(0,K_y/2+1)$ to $(K_x/2,y_{max}-K_y/2-1)$;
Sub-region #5: $(K_x/2+1,K_y/2+1)$ to $(x_{max}-K_x/2-1,y_{max}-K_y/2-1)$;
Sub-region #6: $(x_{max}-K_x/2,K_y/2+1)$ to $(x_{max},y_{max}-K_y/2-1)$;
Sub-region #7: $(0,y_{max}-K_y/2)$ to $(K_x/2,y_{max})$;
Sub-region #8: $(K_x/2+1,y_{max}-K_y/2)$ to $(x_{max}-K_x/2-1,y_{max})$;
Sub-region #9: $(x_{max}-K_x/2,y_{max}-K_y/2)$ to $(x_{max},y_{max})$;
where $K_x$ is the number of columns in the kernel, $K_y$ is the number of rows in the kernel, $x_{max}+1$ and $y_{max}+1$ are the number of columns and rows in said image.

5. The method of claim 4 wherein said processing step includes the following substeps:
for Sub-Regions #1, #2 and #3:
vertical image sum buffers are created for each pixel in the first row of the rectangle-of-interest: the vertical image sum buffer for each column of the image is initialized to the sum of the first $K_y/2$ image pixels in that column;
prior to the calculations for each row in the sub-regions #1, #2 and #3, the vertical image sum buffers are augmented by the image value for that pixel in row $y+K_y/2$;
for Sub-Region #1:
the image accumulator is initialized to the sum of the first $K_x/2+1$ vertical image sum buffers; the pixel count accumulator is initialized to $(K_x/2+1)*(K_y/2+1)$; the output image at the first pixel is the value of the image accumulator divided by the value of the pixel count accumulator;
for pixel x in each line the value of the $x+K_x/2$ vertical image sum buffer is added to the image accumulator and $K_y/2+1+y$ is added to the pixel count accumulator; the output image is the value of the image accumulator divided by the value of the pixel count accumulator;
for Sub-Region #2:
at each successive pixel the value of the $x+K_x/2$ vertical image sum buffer is added and the value of the $x-K_x/2-1$ vertical image sum buffer is subtracted from the image accumulator; the pixel count accumulator is unchanged; the output image is the value of the image accumulator divided by the value of the pixel count accumulator;
for Sub-Region #3:
at each successive pixel the value of the $x-K_x/2-1$ vertical image sum buffer is subtracted from the image accumulator and $K_y/2+1+y$ is subtracted from the pixel count accumulator; the output image is the value of the image accumulator divided by the value of the pixel count accumulator;
for Sub-Regions #4, #5, and #6:
the calculations for these regions are the same as those for regions #1, #2, and #3, respectively, with the following exception;
prior to the calculations for each row in the sub-regions #4, #5 and #6 the vertical image sum buffers are augmented by image pixel value in row $y+K_y/2$ and reduced by the image pixel value in row $y-K_y/2-1$; the pixel count accumulator is adjusted appropriately in each of the three sub-regions;
for Sub-Regions #7, #8, and #9:
the calculations for these regions are the same as those for regions #1, #2, and #3, respectively, with the following exception; prior to the calculations for each row in the sub-regions #7, #8 and #9 the vertical image sum buffers are reduced by the image pixel value in row $y-K_y/2-1$;
for Sub-Region #7:
the image accumulator is initialized to the sum of the first $K_x/2+1$ vertical image sum buffers; the pixel count accumulator is initialized to $(y_{max}-y+K_y/2+1)*(K_x/2+1)$; the output image at the first pixel is the value of the image accumulator divided by the value of the pixel count accumulator;
for pixel x in each line the value of the $x+K_x/2+1$ vertical image sum buffer is added to the image accumulator and the pixel count accumulator is incremented by $y_{max}-y+K_y/2+1$ to reflect the total number of pixels contributing to the convolution;
for Sub-Region #8:
at each successive pixel the value of the $x+K_x/2$ vertical image sum buffer is added and the value of the $x-K_x/2-1$ vertical image sum buffer is subtracted from the image accumulator; the pixel count accumulator is unchanged; the output image is the value of the image accumulator divided by the value of the pixel count accumulator; and
for Sub-Region #9:
at each successive pixel the value of the $x-K_x/2-1$ vertical image sum buffer is subtracted from the image accumulator and $y_{max}-y+K_y/2+1$ is subtracted from the pixel count accumulator; the output image is the value of the image accumulator divided by the value of the pixel count accumulator.

6. A method of analyzing the low- and high-frequency components of an arbitrary connected region of interest within a digital image using uniform kernel comprising the steps of:

partitioning the digital image into nine sub-regions based on the size of said digital image and the size of said kernel;

processing each of said sub-regions using a unique image processing algorithm; and combining said processed sub-regions into a resulting image.

7. A method of analyzing the low- and high-frequency components of an arbitrary connected region of interest within an image using a rectangular uniform kernel described in claim 6 wherein said partitioning is based on Sub-region #1: (0,0) to $(K_x/2,K_y/2)$;
Sub-region #2: $K_x/2+1,0)$ to $(x_{max}-K_x/2-1,K_y/2)$;
Sub-region #3: $(x_{max}-K_x/2,0)$ to $(x_{max},K_y/2)$;
Sub-region #4: $(0,K_y/2+1)$ to $(K_x/2,y_{max}-K_y/2-1)$;
Sub-region #5: $(K_x/2+1,K_y/2+1)$ to $(x_{max}-K_x/2-1,y_{max}-K_y/2-1)$;
Sub-region #6: $(x_{max}-K_x/2,K_y/2+1)$ to $(x_{max},y_{max}-K_y/2-1)$;
Sub-region #7: $(0,y_{max}-K_y/2)$ to $(K_x/2,y_{max})$;
Sub-region #8: $(K_x/2+1,y_{max}-K_y/2)$ to $(x_{max}-K_x/2-1, y_{max})$;
Sub-region #9: $(x_{max}-K_x/2,y_{max}-K_y/2)$ to $(x_{max},y_{max})$;
where $K_x$ is the number of columns in the kernel, $K_y$ is the number of rows in the kernel, $x_{max}+1$ and $y_{max}+1$ are the number of columns and rows in said image.

8. A method of analyzing the low- and high-frequency components of an arbitrary connected region of interest within an image using a rectangular uniform kernel described in claim 7 wherein said processing step includes the following substeps:

Sub-Regions #1, #2 and #3:

vertical pixel count buffers are created for each pixel in the first row of the rectangle-of-interest; the vertical pixel count buffer for each column of the image is initialized to sum of the first $K_y/2$ mask pixels in that column; mask pixels are one within the region of interest and zero otherwise; vertical image sum buffers are created for each pixel in the first row of the rectangle-of-interest; the vertical image sum buffer for each column of the image is initialized to sum of the product of the first $K_y/2$ image pixels in that column each multiplied by the respective mask image value;

prior to the calculations for each row in the sub-regions #1, #2 and #3 the vertical pixel count buffers are augmented by the mask value for that pixel in row $y+K_y/2$ and the vertical image sum buffers are augmented by the product of the image and the mask for that pixel in row $y+K_y/2$;

Sub-Region #1:

the image accumulator is initialize to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;

for pixel x in each line the $x+K_x/2$ vertical image sum buffer and the $x+K_x/2$ vertical pixel count buffer are added to their respective accumulators; the output image is the value of the image accumulator divided by the value of the pixel count accumulator;

Sub-Region #2:

at each successive pixel the $x+K_x/2$ vertical image sum buffer and the $x+K_x/2$ vertical pixel count buffer are added to their respective accumulators; the $x-K/2-1$ vertical image sum buffer and the $x-K_x/2-1$ vertical pixel count buffer are subtracted from their respective accumulators; the output image is the value of the image accumulator divided by the value of the pixel count accumulator;

Sub-Region #3:

at each successive pixel the $x-K_x/2-1$ vertical image sum buffer and the $x-K_x/2-1$ vertical pixel count buffer are subtracted from their respective accumulators; the output image is the value of the image accumulator divided by the value of the pixel count accumulator;

Sub-Regions #4, #5, and #6:

the calculations for these regions are the same as those for regions #1, #2, and #3, respectively, with the following exception;

prior to the calculations for each row in the sub-regions #4, #5 and #6 the vertical image sum buffers are augmented by image pixel value in row $y+K_y/2$ and reduced by the image pixel value in row $y-K_y/2-1$; the pixel count accumulator is adjusted appropriately in each of the three sub-regions;

Sub-Regions #7, #8, and #9:

the calculations for these regions are the same as those for regions #1, #2, and #3, respectively, with the following exception; prior to the calculations for each row in the sub-regions #7, #8 and #9 the vertical image sum buffers are reduced by the product of the image pixel value and the mask value in row $y-K_y/2-1$, and the pixel sum buffers are reduced by the mask value in row $y-K_y/2-1$;

Sub-Region #7:

the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;

for pixel x in each line the value of the $x+K_x/2+1$ vertical image sum buffer is added to the image accumulator and the $x+K_x/2+1$ vertical pixel count buffer is added to the pixel count accumulator to reflect the total number of pixels contributing to the convolution;

Sub-Region #8:

at each successive pixel, the value of the $x+K_x/2$ vertical image sum buffer is added and the value of the $x-K_x/2-1$ vertical image sum buffer is subtracted from the image accumulator and the $x+K_x/2$ vertical pixel count buffer is added and the value of the $x-K_x/2-1$ vertical pixel count buffer is subtracted from the pixel count accumulator; the output image is the value of the image accumulator divided by the value of the pixel count accumulator;

Sub-Region #9:

at each successive pixel, the value of the $x-K_x/2-1$ vertical image sum buffer is subtracted from the image accumulator and the value of the $x-K_x/2-1$ vertical pixel count buffer is subtracted from the pixel count accumulator; the output image is the value of the image accumulator divided by the value of the pixel count accumulator.

9. A method of analyzing the low- and high-frequency components of an arbitrary connected region of interest within a digital image using a kernel comprising the steps of:
   defining the rectangular bounding box for the region of interest;
   partitioning the digital image within the bounding box into nine sub-regions based on the sizes of said digital image and said boundary box;
   processing each of said sub-regions using a unique image processing algorithm;
   combining said processed sub-regions into a resulting image.

10. A method of analyzing the low- and high-frequency components of an arbitrary connected region of interest within an image using a rectangular uniform kernel described in claim 9 wherein the region of interest is analyzed to find the first image line ($y_{min}$) and fast image line ($y_{max}$) within the region of interest as well as the first image pixel ($x_{min}$) and last image pixel ($x_{max}$) on any line within the region of interest and these then define the rectangle-of-interest, a rectangular bounding box, that includes the entire region of interest having corners at ($x_{min}, y_{min}$), and ($x_{max}, y_{max}$).

11. A method of analyzing the low- and high-frequency components of an arbitrary connected region of interest within an image using a rectangular uniform kernel described in claim 10 wherein said partitioning is based on:
   Sub-region #1: ($x_{min}, y_{min}$) to ($x_{min}+K_x/2, y_{min}+K_y/2$);
   Sub-region #2: ($X_{min}+K_x/2+1, y_{min}$) to ($x_{max}-K_x/2-1, y_{min}+K_y/2$);
   Sub-region #3: ($x_{max}-K_x/2, y_{min}$) to ($x_{max}, y_{min}+K_y/2$);
   Sub-region #4: ($x_{min}, y_{min}+K_y/2+1$) to ($x_{min}+K_x/2, y_{max}-K_y/2-1$);
   Sub-region #5: ($x_{min}+K_x/2+1, y_{min}+K_y/2+1$) to ($x_{max}-K_x/2-1, y_{max}-K_y/2-1$);
   Sub-region #6: ($x_{max}-K_x/2, y_{min}+K_y/2+1$) to ($x_{max}, y_{max}-K_y/2-1$);
   Sub-region #7: ($x_{min}, y_{max}-K_y/2$) to ($x_{min}+K_x/2, y_{max}$);
   Sub-region #8: ($x_{min}+K_x/2+1, y_{max}-K_y/2$) to ($x_{max}-K_x/2-1, y_{max}$);
   Sub-region #9: ($x_{max}-K_x/2, y_{max}-K_y/2$) to ($x_{max}, y_{max}$);
   where $K_x$ is the number of columns in the kernel, $K_y$ is the number of rows in the kernel, ($x_{min}, y_{min}$), and ($x_{max}, y_{max}$) define the opposite corners of a rectangle-of-interest that includes the entire region of interest.

12. A method of analyzing the low- and high-frequency components of an arbitrary connected region of interest within an image using a rectangular uniform kernel described in claim 11 wherein said processing step includes the following substeps:
   Sub-Regions #1, #2 and #3:
      vertical pixel count buffers are created for each pixel in the first row of the rectangle-of-interest; the vertical pixel count buffer for each column of the image is initialized to sum of the first $K_y/2$ mask pixels in that column; mask pixels are one within the region of interest and zero otherwise; vertical image sum buffers are created for each pixel in the first row of the rectangle-of-interest; the vertical image sum buffer for each column of the image is initialized to sum of the product of the first $K_y/2$ image pixels in that column each multiplied by the respective mask image value;
      prior to the calculations for each row in the sub-regions #1, #2 and #3, the vertical pixel count buffers are augmented by the mask value for that pixel in row $y+K_y/2$ and the vertical image sum buffers are augmented by the product of the image and the mask for that pixel in row $y+K_y/2$;
   Sub-Region #1:
      the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;
      for pixel x in each line the $x+K_x/2$ vertical image sum buffer and the $x+K_x/2$ vertical pixel count buffer are added to their respective accumulators; the output image is the value of the image accumulator divided by the value of the pixel count accumulator;
   Sub-Region #2:
      at each successive pixel the $x+K_x/2$ vertical image sum buffer and the $x+K_x/2$ vertical pixel count buffer are added to their respective accumulators; the $x-K_x/2-1$ vertical image sum buffer and the $x-K_x/2-1$ vertical pixel count buffer are subtracted from their respective accumulators; the output image is the value of the image accumulator divided by the value of the pixel count accumulator;
   Sub-Region #3:
      at each successive pixel the $x-K_x/2-1$ vertical image sum buffer and the $x-K_x/2-1$ vertical pixel count buffer are subtracted from their respective accumulators; the output image is the value of the image accumulator divided by the value of the pixel count accumulator;
   Sub-Regions #4, #5, and #6:
      the calculations for these regions are the same as those for regions #1, #2, and #3, respectively, with the following exception: prior to the calculations for each row in the sub-regions #4, #5 and #6, the vertical image sum buffers are augmented by the image pixel value in row $y+K_y/2$ and reduced by the image pixel value in row $y-K_y/2-1$, and the vertical pixel count buffers are augmented by the mask pixel value in row $y+K_y/2$ and reduced by the mask pixel value in row $y-K_y/2-1$;
   Sub-Regions #7, #8, and #9:
      the calculations for these regions are the same as those for regions #1, #2, and #3, respectively, with the following exception: prior to the calculations for each row in the sub-regions #7, #8 and #9, the vertical image sum buffers are reduced by the product of the image pixel value in row $y-K_y/2-1$ and the corresponding mask pixel value, and the pixel sum buffers are reduced by the mask pixel value in row $y-K_y/2-1$;
   Sub-Region #7:
      the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;
      for pixel x in each line the value of the $x+K_x/2+1$ vertical image sum buffer is added to the image accumulator and the $x+K_x/2+1$ vertical pixel count buffer is added to the pixel count accumulator to reflect the total number of pixels contributing to the convolution;

Sub-Region #8:
  at each successive pixel, the value of the $x+K_x/2$ vertical image sum buffer is added and the value of the $x-K_x/2-1$ vertical image sum buffer is subtracted from the image accumulator; also the value of the $x+K_x/2$ vertical pixel count buffer is added and the value of the $x-K_x/2-1$ vertical pixel count buffer is subtracted from the pixel count accumulator; the output image is the value of the image accumulator divided by the value of the pixel count accumulator;

Sub-Region #9:
  at each successive pixel, the value of the $x-K_x/2-1$ vertical image sum buffer is subtracted from the image accumulator and the value of the $x-K_x/2-1$ vertical pixel count buffer is subtracted from the pixel count accumulator; the output image is the value of the image accumulator divided by the value of the pixel count accumulator.

13. A method of analyzing the low- and high-frequency components of an arbitrary connected region of interest within a digital image using a rectangular uniform kernel comprising the steps of:
  preprocessing the digital image with mask data;
  partitioning the digital image into nine sub-regions based on said mask data and the sizes of said digital image and said kernel;
  processing each of said sub-regions using a unique image processing algorithm; and
  combining said processed sub-regions into a resulting image.

14. A method of analyzing the low- and high-frequency components of an arbitrary connected region of interest within an image using a rectangular uniform kernel described in claim 13 wherein each pixel of the image is multiplied by the value of a mask image where the mask image has a value of one in the region of interest and zero otherwise.

15. A method of analyzing the low- and high-frequency components of an arbitrary connected region of interest within an image using a rectangular uniform kernel described in claim 14 wherein said partitioning is based on:
  Sub-region #1: $(0,0)$ to $(K_x/2,K_y/2)$;
  Sub-region #2: $(K_x/2+1,0)$ to $(x_{max}-K_x/2-1,K_y/2)$;
  Sub-region #3: $(x_{max}-K_x/2,0)$ to $(x_{max},K_y/2)$;
  Sub-region #4: $(0,K_y/2+1)$ to $(K_x/2,y_{max}-K_y/2-1)$;
  Sub-region #5: $(K_x/2+1,K_y/2+1)$ to $(x_{max}-K_x/2-1,y_{max}-K_y/2-1)$;
  Sub-region #6: $(x_{max}-K_x/2,K_y/2+1)$ to $(x_{max},y_{max}-K_y/2-1)$;
  Sub-region #7: $(0,y_{max}-K_y/2)$ to $(K_x/2,y_{max})$;
  Sub-region #8: $(K_x/2+1,y_{max}-K_y/2)$ to $(x_{max}-K_x/2-1,y_{max})$;
  Sub-region #9: $(x_{max}-K_x/2,y_{max}-K_y/2)$ to $(x_{max},y_{max})$;
  where $K_x$ is the number of columns in the kernel, $K_y$ is the number of rows in the kernel, $x_{max}+1$ and $y_{max}+1$ are the number of columns and rows in said image.

16. A method of analyzing the low- and high-frequency components of an entire image using a rectangular uniform kernel described in claim 15 wherein said processing step includes the following substeps:
  Sub-Regions #1, #2 and #3:
    vertical image sum buffers and vertical pixel sum buffers are created for each pixel in the first row of the rectangle-of-interest; the vertical pixel count buffer for each column of the image is initialized to sum of the first $K_y/2$ mask pixels in that column; mask pixels are one within the region of interest and zero otherwise; the vertical image sum buffer for each column of the image is initialized to sum of the first $K_y/2$ image pixel values in that column;
    prior to the calculations for each row in the sub-regions #1, #2 and #3, the vertical pixel count buffers are augmented by the mask value for that pixel in row $y+K_y/2$ and the vertical image sum buffers are augmented by the image pixel values for that column in row $y+K_y/2$;
  Sub-Region #1:
    the image accumulator is initialized to the sum of the first $K_x/2+1$ vertical image sum buffers; the pixel count accumulator is initialized to the sum of the first $K/2+1$ vertical pixel count buffers; the output image at the first pixel is the value of the image accumulator divided by the value of the pixel count accumulator;
    for pixel x in each line the $x+K_x/2$ vertical image sum buffer and the $x+K_x/2$ vertical pixel count buffer are added to their respective accumulators; the output image is the value of the image accumulator divided by the value of the pixel count accumulator;
  Sub-Region #2:
    at each successive pixel, the $x+K_x/2$ vertical image sum buffer and the $x+K_x/2$ vertical pixel count buffer are added to their respective accumulators; the $x-K_x/2-1$ vertical image sum buffer and the $x-K_x/2-1$ vertical pixel count buffer are subtracted from their respective accumulators; the output image is the value of the image accumulator divided by the value of the pixel count accumulator;
  Sub-Region #3:
    at each successive pixel the $x-K_x/2-1$ vertical image sum buffer and the $x-K_x/2-1$ vertical pixel count buffer are subtracted from their respective accumulators; the output image is the value of the image accumulator divided by the value of the pixel count accumulator;
  Sub-Regions #4, #5, and #6:
    the calculations for these regions are the same as those for regions #1, #2, and #3, respectively, with the following exception;
    prior to the calculations for each row in the sub-regions #4, #5 and #6, the vertical image sum buffers are augmented by image pixel value in row $y+K_y/2$ and reduced by the image pixel value in row $y-K_y/2-1$, and the vertical pixel count buffers are augmented by mask pixel value in row $y+K_y/2$ and reduced by the mask pixel value in row $y-K_y/2-1$;
    the pixel count accumulator is adjusted appropriately in each of the three sub-regions;
  Sub-Regions #7, #8, and #9:
    the calculations for these regions are the same as those for regions #1, #2, and #3, respectively, with the following exception: prior to the calculations for each row in the sub-regions #7, #8 and #9, the vertical image sum buffers are reduced by the image pixel value in row $y-K_y/2-1$, and the pixel sum buffers are reduced by the mask pixel value in row $y-K_y/2-1$;
  Sub-Region #7:
    the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;

for pixel x in each line the value of the $x+K_x/2+1$ vertical image sum buffer is added to the image accumulator and the $x+K_x/2+1$ vertical pixel count buffer is added to the pixel count accumulator to reflect the total number of pixels contributing to the convolution;

Sub-Region #8:

at each successive pixel, the value of the $x+K_x/2$ vertical image sum buffer is added and the value of the $x-K_x/2-1$ vertical image sum buffer is subtracted from the image accumulator; also the value of the $x+K_x/2$ vertical pixel count buffer is added and the value of the $x-K_x/2-1$ vertical pixel count buffer is subtracted from the pixel count accumulator; the output image is the value of the image accumulator divided by the value of the pixel count accumulator;

Sub-Region #9:

at each successive pixel, the value of the $x-K_x/2-1$ vertical image sum buffer is subtracted from the image accumulator and the value of the $x-K_x/2-1$ vertical pixel count buffer is subtracted from the pixel count accumulator; the output image is the value of the image accumulator divided by the value of the pixel count accumulator.

17. A method of analyzing the low- and high-frequency components of an arbitrary connected region of interest within a digital image using a kernel comprising the steps of:

defining the rectangular bounding box for the region of interest;

preprocessing the digital image within the bounding box with the mask data;

partitioning the image within the bounding box into nine sub-regions based on the size of said bounding box and said mask data;

processing each of said sub-regions using a unique image processing algorithm;

combining said processed sub-regions into a resulting image.

18. A method of analyzing the low- and high-frequency components of an arbitrary connected region of interest within an image using a rectangular uniform kernel described in claim 17 wherein the region of interest is analyzed to find the first line ($y_{min}$) and last image line ($y_{max}$) within the region of interest as well as the first pixel ($x_{min}$) and last pixel ($x_{max}$) on any line within the region of interest and these then define the rectangle-of-interest, a rectangular bounding box, that includes the entire region of interest having corners at ($x_{min}, y_{min}$), and ($x_{max}, y_{max}$).

19. A method of analyzing the low- and high-frequency components of an arbitrary connected region of interest within an image using a rectangular uniform kernel described in claim 18 wherein each pixel of the image within the bounding box is multiplied by the value of the mask image where the mask image has a value of one in the region of interest and zero otherwise.

20. A method of analyzing the low- and high-frequency components of an arbitrary connected region of interest within an image using a rectangular uniform kernel described in claim 18, wherein in said partitioning step each sub-region is defined as follows:

Sub-region #1: ($x_{min}, y_{min}$) to ($x_{min}+K_x/2, y_{min}+K_y/2$);
Sub-region #2: ($x_{min}+K_x/2+1, y_{min}$) to ($x_{min}-K_x/2-1, y_{min}+K_y/2$);
Sub-region #3: ($x_{min}-K_x/2, y_{min}$) to ($x_{max}, y_{min}+K_y/2$);
Sub-region #4: ($x_{min}, y_{min}+K_y/2+1$) to ($x_{min}+K_x/2, y_{max}-K_y/2-1$);
Sub-region #5: ($x_{min}+K_x/2+1, y_{min}+K_y/2+1$) to ($x_{max}-K_x/2-1, y_{max}-K_y/2-1$);
Sub-region #6: ($x_{max}-K_x/2, y_{min}+K_y/2+1$) to ($x_{max}, y_{max}-K_y/2-1$);
Sub-region #7: ($x_{max}, y_{max}-K_y/2$) to ($x_{min}+K_x/2, y_{max}$);
Sub-region #8: ($x_{min}+K_x/2+1, y_{max}-K_y/2$) to ($x_{max}-K_x/2-1, y_{max}$);
Sub-region #9: ($x_{max}-K_x/2, y_{max}-K_y/2$) to ($x_{max}, y_{max}$);

where $K_x$ is the number of columns in the kernel, $K_y$ is the number of rows in the kernel, ($x_{min}, y_{min}$), and ($x_{max}, y_{max}$) define the opposite corners of a rectangle-of-interest that includes the entire region of interest.

21. A method of analyzing the low- and high-frequency components of an arbitrary connected region of interest within an image using a rectangular uniform kernel described in claim 20 wherein said processing step includes the following substeps:

Sub-Regions #1, #2 and #3:

vertical pixel count buffers are created for each pixel in the first row of the rectangle-of-interest; the vertical pixel count buffer for each column of the image is initialized to sum of the first $K_y/2$ mask pixels in that column; mask pixels are one within the region of interest and zero otherwise; vertical image sum buffers are created for each pixel in the first row of the rectangle-of-interest; the vertical image sum buffer for each column of the image is initialized to sum of the product of the first $K_y/2$ image pixels in that column each multiplied by the respective mask image value;

prior to the calculations for each row in the sub-regions #1, #2 and #3, the vertical pixel count buffers are augmented by the mask value for that pixel in row $y+K_y/2$ and the vertical image sum buffers are augmented by the product of the image and the mask for that pixel in row $y+K_y/2$;

Sub-Region #1:

the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;

for pixel x in each line the $x+K_x/2$ vertical image sum buffer and the $x+K_x/2$ vertical pixel count buffer are added to their respective accumulators; the output image is the value of the image accumulator divided by the value of the pixel count accumulator;

Sub-Region #2:

at each successive pixel, the $x+K_x/2$ vertical image sum buffer and the $x+K_x/2$ vertical pixel count buffer are added to their respective accumulators; the $x-K_x/2-1$ vertical image sum buffer and the $x-K_x/2-1$ vertical pixel count buffer are subtracted from their respective accumulators; the output image is the value of the image accumulator divided by the value of the pixel count accumulator;

Sub-Region #3:

at each successive pixel, the $x-K_x/2-1$ vertical image sum buffer and the $x-K_x/2-1$ vertical pixel count buffer are subtracted from their respective accumulators; the output image is the value of the image accumulator divided by the value of the pixel count accumulator;

Sub-Regions #4, #5, and #6:
    the calculations for these regions are the same as those for regions #1, #2, and #3, respectively, with the following exception;
    prior to the calculations for each row in the sub-regions #4, #5 and #6, the vertical image sum buffers are augmented by image pixel value in row $y+K_y/2$ and reduced by the image pixel value in row $y-K_y/2-1$, and the vertical pixel count buffers are augmented by mask pixel value in row $y+K_y/2$ and reduced by the mask pixel value in row $y-K_y/2-1$;

Sub-Regions #7, #8, and #9:
    the calculations for these regions are the same as those for regions #1, #2, and #3, respectively, with the following exception: prior to the calculations for each row in the sub-regions #7, #8 and #9, the vertical image sum buffers are reduced by the product of the image pixel value in row $y-K_y/2-1$ and the corresponding mask pixel value, and the pixel sum buffers are reduced by the mask pixel value in row $y-K_y/2-1$;

Sub-Region #7:
    the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;
    for pixel x in each line the value of the $x+K_x/2+1$ vertical image sum buffer is added to the image accumulator and the $x+K_x/2+1$ vertical pixel count buffer is added to the pixel count accumulator to reflect the total number of pixels contributing to the convolution;

Sub-Region #8:
    at each successive pixel, the value of the $x+K_x/2$ vertical image sum buffer is added and the value of the $x-K_x/2-1$ vertical image sum buffer is subtracted from the image accumulator; also the value of the $x+K_x/2$ vertical pixel count buffer is added and the value of the $x-K_x/2-1$ vertical pixel count buffer is subtracted from the pixel count accumulator; the output image is the value of the image accumulator divided by the value of the pixel count accumulator;

Sub-Region #9:
    at each successive pixel, the value of the $x-K_x/2-1$ vertical image sum buffer is subtracted from the image accumulator and the value of the $x-K_x/2-1$ vertical pixel count buffer is subtracted from the pixel count accumulator; the output image is the value of the image accumulator divided by the value of the pixel count accumulator.

22. A method of analyzing the low- and high-frequency components of multiple non-overlapping but otherwise arbitrary connected regions of interest within a digital image using a kernel comprising the steps of:
    defining the rectangular bounding box for each region of interest from which an intermediate image is derived;
    partitioning each intermediate image within its bounding box into nine sub-regions based on the size of the bounding box and size of the kernel;
    processing each of said sub-regions using a unique image processing algorithm; and
    combining said processed sub-regions into a resulting intermediate images for each region of interest.

23. A method of analyzing the low- and high-frequency components of multiple non-overlapping but otherwise arbitrary connected regions of interest within an image using a rectangular uniform kernel described in claim 22 wherein the region of interest is analyzed to find the first line ($y_{min}$) and last image line ($y_{max}$) within the region of interest as well as the first pixel ($x_{min}$) and last pixel ($x_{max}$) on any line within the region of interest, and these then define the rectangle-of-interest, a rectangular bounding box, that includes the said region of interest having corners at ($x_{min}$, $y_{min}$), and ($x_{max}$, $y_{max}$).

24. A method of analyzing the low- and high-frequency components of multiple non-overlapping but otherwise arbitrary connected regions of interest within each intermediate image using a rectangular uniform kernel described in claim 23 wherein each pixel of the image is multiplied by the value of a mask image where the mask image has a value of one in the region of interest and zero otherwise.

25. A method of analyzing the low- and high-frequency components of multiple non-overlapping but otherwise arbitrary connected regions of interest within each intermediate image using a rectangular uniform kernel described in claim 23 wherein in said partitioning step each sub-region is defined as follows:

Sub-region #1: ($x_{min}, y_{min}$) to ($x_{min}+K_x/2, y_{min}+K_y/2$);
    Sub-region #2: ($x_{min}+K_x/2+1, y_{min}$) to ($x_{max}-K_x/2-1, y_{min}+K_y/2$);
    Sub-region #3: ($x_{max}-K_x/2, y_{min}$) to ($x_{max}, y_{min}+K_y/2$);
    Sub-region #4: ($x_{min}, y_{min}+K_y/2+1$) to ($x_{min}+K_x/2, y_{max}-K_y/2-1$);
    Sub-region #5: ($x_{min}+K_x/2+1, y_{min}+K_y/2+1$) to ($x_{max}-K_x/2-1, y_{max}-K_y/2-1$);
    Sub-region #6: ($x_{max}-K_x/2, y_{min}+K_y/2+1$) to ($x_{max}, y_{max}-K_y/2-1$);
    Sub-region #7: ($x_{min}, y_{max}-K_y/2$) to ($x_{min}+K_x/2, y_{max}$);
    Sub-region #8: ($x_{min}+K_x/2+1, y_{max}-K_y/2$) to ($x_{max}-K_x/2-1, y_{max}$);
    Sub-region #9: ($x_{max}-K_x2, y_{max}-K_y/2$) to ($x_{max}, y_{max}$);
    where $K_x$ is the number of columns in the kernel, $K_y$ is the number of rows in the kernel, ($x_{min}, y_{min}$) and ($x_{max}, y_{max}$) define the opposite corners of a rectangle-of-interest that includes the entire region of interest.

26. A method of analyzing the low- and high-frequency components of multiple non-overlapping but otherwise arbitrary connected regions of interest within each intermediate image using a rectangular uniform kernel described in claim 25 wherein said processing includes the following substeps:

Sub-Regions #1, #2 and #3:
        vertical pixel count buffers are created for each pixel in the first row of the rectangle-of-interest; the vertical pixel count buffer for each column of the image is initialized to sum of the first $K_y/2$ mask pixels in that column; mask pixels are one within the region of interest and zero otherwise; vertical image sum buffers are created for each pixel in the first row of the rectangle-of-interest; the vertical image sum buffer for each column of the image is initialized to sum of the product of the first $K_y/2$ image pixels in that column each multiplied by the respective mask image value;
        prior to the calculations for each row in the sub-regions #1, #2 and #3, the vertical pixel count buffers are augmented by the mask value for that pixel in row $y+K_y/2$ and the vertical image sum buffers are augmented by the product of the image and the mask for that pixel in row $y+K_y/2$;

Sub-Region #1:
  the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;
  for pixel x in each line the $x+K_x/2$ vertical image sum buffer and the $x+K_x/2$ vertical pixel count buffer are added to their respective accumulators; the output image is the value of the image accumulator divided by the value of the pixel count accumulator;

Sub-Region #2:
  at each successive pixel the $x+K_x/2$ vertical image sum buffer and the $x+K_x/2$ vertical pixel count buffer are added to their respective accumulators; the $x-K_x/2-1$ vertical image sum buffer and the $x-K_x/2-1$ vertical pixel count buffer are subtracted from their respective accumulators; the output image is the value of the image accumulator divided by the value of the pixel count accumulator;

Sub-Region #3:
  at each successive pixel the $x-K_x/2-1$ vertical image sum buffer and the $x-K_x/2-1$ vertical pixel count buffer are subtracted from their respective accumulators; the output image is the value of the image accumulator divided by the value of the pixel count accumulator;

Sub-Regions #4, #5, and #6:
  the calculations for these regions are the same as those for regions #1, #2, and #3, respectively, with the following exception: prior to the calculations for each row in the sub-regions #4, #5 and #6 the vertical image sum buffers are augmented by image pixel value in row $y+K_y/2$ and reduced by the image pixel value in row $y-K_y/2-1$, and the vertical pixel count buffers are augmented by mask pixel value in row $y+K_y/2$ and reduced by the mask pixel value in row $y-K_y/2-1$;

Sub-Regions #7, #8, and #9:
  the calculations for these regions are the same as those for regions #1, #2, and #3, respectively, with the following exception: prior to the calculations for each row in the sub-regions #7, #8 and #9, the vertical image sum buffers are reduced by the product of the image pixel value in row $y-K_y/2-1$ and the corresponding mask pixel value, and the pixel sum buffers are reduced by the mask pixel value in row $y-K_y/2-1$;

Sub-Region #7:
  the image accumulator is initialized to the sum of the first $K_x/2+1$ vertical image sum buffers; the pixel count accumulator is initialized to the sum of the first $K_x/2+1$ vertical pixel count buffers; the output image at the first pixel is the value of the image accumulator divided by the value of the pixel count accumulator;
  for pixel x in each line, the value of the $x+K_x/2+1$ vertical image sum buffer is added to the image accumulator, and the $x+K_x/2+1$ vertical pixel count buffer is added to the pixel count accumulator to reflect the total number of pixels contributing to the convolution;

Sub-Region #8:
  at each successive pixel, the value of the $x+K_x/2$ vertical image sum buffer is added and the value of the $x-K_x/2-1$ vertical image sum buffer is subtracted from the image accumulator; also the value of the $x+K_x/2$ vertical pixel count buffer is added and the value of the $x-K_x/2-1$ vertical pixel count buffer is subtracted from the pixel count accumulator; the output image is the value of the image accumulator divided by the value of the pixel count accumulator;

Sub-Region #9:
  at each successive pixel, the value of the $x-K_x/2-1$ vertical image sum buffer is subtracted from the image accumulator and the value of the $x-K_x/2-1$ vertical pixel count buffer is subtracted from the pixel count accumulator; the output image is the value of the image accumulator divided by the value of the pixel count accumulator.

* * * * *